United States Patent [19]

Marsoner et al.

[11] Patent Number: 4,587,101
[45] Date of Patent: May 6, 1986

[54] MEASURING DEVICE FOR DETERMINING THE $O_2$ CONTENT OF A SAMPLE

[75] Inventors: Hermann Marsoner; Herbert Kroneis, both of Graz, Austria

[73] Assignee: AVL AG, Schaffhausen, Switzerland

[21] Appl. No.: 553,386

[22] Filed: Nov. 18, 1983

[30] Foreign Application Priority Data

Nov. 22, 1982 [AT] Austria ................................ 4248/82

[51] Int. Cl.$^4$ .......................... G01N 1/48; G01N 21/06
[52] U.S. Cl. ........................................ 422/56; 436/172; 250/462.1; 428/690; 252/408.1
[58] Field of Search ...................... 428/690; 250/462.1; 252/408.1; 422/52, 56; 436/136, 138, 172

[56] References Cited

U.S. PATENT DOCUMENTS

| | | | |
|---|---|---|---|
| 2,907,882 | 10/1959 | Patten | 428/690 X |
| 3,776,761 | 12/1973 | Kato et al. | 428/690 X |
| 4,003,707 | 1/1977 | Lübbers | 436/172 |
| 4,409,277 | 10/1983 | Michel | 428/690 X |

FOREIGN PATENT DOCUMENTS

| | | | |
|---|---|---|---|
| 2508637 | 11/1979 | Fed. Rep. of Germany. | |
| 575639 | 5/1976 | Switzerland | 250/462.1 |

Primary Examiner—George F. Lesmes
Assistant Examiner—Nancy A. B. Swisher
Attorney, Agent, or Firm—Watson, Cole, Grindle & Watson

[57] ABSTRACT

In a sensor element for determining the $O_2$ content of a sample, comprising a fluorescent indicator substance which is embedded in a polymer carrier and with which the sample may be brought into contact, a fluorescence extinction sufficiently high for yielding useful measurement results is achieved by the use of plasticizer-compatible polymers as carrier materials which contain plasticizers in addition to the indicator molecules.

15 Claims, 1 Drawing Figure

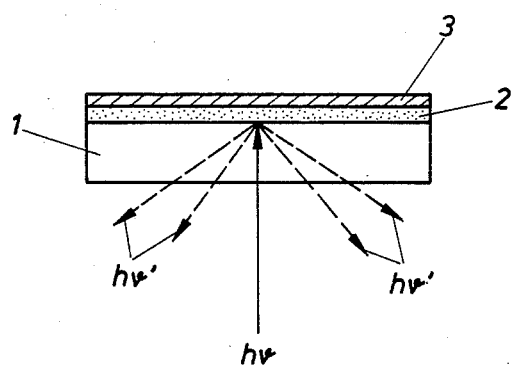

MEASURING DEVICE FOR DETERMINING THE O₂ CONTENT OF A SAMPLE

BACKGROUND OF THE INVENTION

This invention relates to a measuring device for determining the O₂ content of a sample, comprising an indicator substance fluorescing with the amount of O₂ acting upon it, which is embedded in a polymer carrier and with which the sample may be brought into contact at least partially, and a set-up for measuring the fluorescent light given off by the indicator substance upon excitation.

DESCRIPTION OF THE PRIOR ART

It is known that molecular oxygen will influence the intensity of fluorescence of a large number of organic substances, e.g., polycyclic aromatic hydrocarbons. In such cases the molecular oxygen will interact with the molecule activated by the excitation light, drawing energy from the excited molecule and reducing the intensity of the fluorescent light emitted. It is also known that the partial pressure of the molecular oxygen may be measured via the fluorescence intensity of such an indicator substance. The fluorescent material may be supplied in a solvent. The partial pressure of the oxygen contained in this solvent will determine the degree of fluorescence intensity.

In a known device, e.g., described in German Pat. No. 25 08 637, a thin film of the indicator solution is applied on a suitable transparent carrier material, and the fluorescent solution is covered by an oxygen-permeable membrane. On the carrier side of this set-up a lighting and light measuring device are located. The thin oxygen-permeable membrane will permit rapid equalization of the partial oxygen pressure in the fluorescent layer and the adjoining medium outside the cover membrane. In the fluorescent layer diffusion will quickly produce the partial oxygen pressure of the adjoining medium, and the intensity of the fluorescent light of the layer will vary accordingly. With this kind of arrangement partial oxygen pressures may be measured by optical means even in aqueous media.

The noted German patent also proposes "leakproof" encapsulation of the indicator substance, i.e., the fluorescent material, in polymer foil. However it does not indicate any method of producing such sensor elements.

Before further discussion of the problem of incorporating indicator molecules into polymers, a list will be given of the major aromatic hydrocarbons which may be used as indicators in a device according to the invention. Among those most preferable are:

Carbazole, acridone, fluoranthene, 9,10-diphenylanthracene, chrysene, benz(a)anthracene, tetracene, pyrene, dibenz(ah)anthracene, perylene, benzo(ghi)perylene, coronene, anthanthrene, decacyclene, 1-aminoanthracene, 2-aminoanthracene, 1-aminopyrene.

In addition, many other fluorescent substances from the group of polycyclic, homocyclic or heterocyclic aromatic hydrocarbons will show fluorescence or extinction of fluorescence upon the influence of molecular oxygen.

Indicator substances of the above type may be incorporated into a polymer by one of the following conventional methods:

(1) Indicator substances are chosen such that they are themselves soluble in the particular polymer solvent. One common solution is then prepared of the indicator substance and the polymer. After evaporation of the common solvent, the polymer containing the indicator substance will remain.

(2) Apart from a common solvent, a polymer suspending agent may be used, provided that this agent is again suited as a solvent for the indicator substance.

(3) If polymerization of the employed polymer is taking place in a reaction mixture of several components, one of these components may be used as a solvent for the indicator substance at the same time.

This simple, conventional method entails a number of problems, making indicator molecules which are incorporated into polymers in this manner unsuited for the purpose of the present invention. For example, evaporation of the common solvent will not lead to a molecular distribution of the indicator substance in the polymer, but will cause the indicator substance to crystallize out in the polymer. Although the crystallized indicator substance in the polymer will show fluorescence, this fluorescence will not be influenced—at least not to any useful degree—by the presence of molecular oxygen.

Besides a fine distribution of microcrystals in the polymer, larger aggregates of crystalline indicator substance were observed to build up in the polymer.

Even if there is a molecular distribution of the indicator substance in the polymer, which may be noted in certain cases, e.g., with PVC solutions, the indicators incorporated in this manner will show no fluorescence extinction due to molecular oxygen.

SUMMARY OF THE INVENTION

It is an object of the present invention to design a measuring device of the aforementioned type such that the above disadvantages of the known devices may be eliminated, and that an extinction of fluorescence may be achieved which is large enough to be used for measurement purposes.

According to the present invention this is achieved by the use of plasticizer-compatible, mostly linear and amorphous polymers as carrier materials for the indicator substance, which contain plasticizers in addition to the embedded indicator molecules. A sufficient degree of fluorescence extinction of the indicator molecules in the polymer will therefore occur if the mixture of polymer and indicator substance contains additional components, i.e., so-called plasticizers. These are compounds which are added to a polymer in order to reduce its brittleness or to increase its flexibility. They act like solvents penetrating the polymer and reducing intermolecular cohesion.

The suitability of a polymer for the purpose of the present invention, e.g., for use as a polymer membrane, is mainly determined by its oxygen permeability, which should be sufficiently high. Sensitivity to oxygen is determined by the fluorescence decay time of the indicator substance used, and by the oxygen permeability coefficient ($P_{O_2}$) of the polymer material. Fluorescence decay time is the average duration of the excited state of a fluorescent molecule.

With the exception of silicone ($P_{O_2} \cong 600 \cdot 10^{-10} \text{cm}^2 \text{s}^{-1} \text{cmHg}^{-1}$), the oxygen permeability coefficients of unplasticized polymers are too low ($P_{O_2} < 35 \cdot 10^{-10} \text{cm}^2 \text{s}^{-1} \text{cmHg}^{-1}$), and do not yield useful results with regard to oxygen sensitivity, even if the fluorescence decay times of the indicator substances used are long.

As a rule, plasticizers to be used for the purposes of the present invention should meet the following requirements:

(1) Compatibility with the polymer
(2) Efficiency
(3) Permanent incorporation into the polymer, and stability of properties over time, i.e., the plasticizer substances should be non-volatile, and should not be extractable by liquids with which the polymer may come into contact.

In a further development of the invention it is therefore proposed that hydrophilic polymers from the group of cellulose acetate, cellulose acetate butyrate, cellulose nitrate or ethyl cellulose be used as carrier materials, and that plasticizers should be chosen from the group of glycol, glycerin or pentalrythrite, or rather that hydrophobic polymers from the group of polyvinyl chloride, polystyrene, polyvinyl acetate, polyvinyl butyral, polyvinyl chloride acetate, polyethylene, polypropylene, polyurethane, polyester, natural rubber, isoprene rubber, chloroprene rubber or butyl rubber, should be chosen as carriers, while plasticizers should be high-boiling esters—such as triarylphosphates, dialkylphthalates, dialkyladipates, dialkylsebacates—mineral oils, chlorinated biphenyls or polyphenyls, epoxidized oils, polymeric plasticizers—such as polyester, polyisobutene, nitride rubber—or polymerizable plasticizers—such as alkyl ester, aryl ester, nitride ester.

Permeability may also be raised by so-called "inner plastification", i.e., chemical modification of the polymer or co-polymerization with other monomers.

In all cases, $O_2$-permeability is increased by the addition of a plasticizer to the polymer; the extent of this increase will depend on the type and amount of plasticizer used. A greater amount of plasticizer will lead to greater permeability. Which type of plasticizer should be chosen will depend on its viscosity. Low-viscosity plasticizers will increase permeability to a greater extent.

In an enhanced form of the present invention polycyclic, homocyclic or heterocyclic aromatic molecules, preferably polycyclic aromatic hydrocarbons with fluorescence decay times $\tau_o$ greater than 5 ns, are used as indicator substances, leading to particularly good results with regard to signal yield.

Like electrochemical sensors for measurement of gases, optical sensors must be calibrated with calibrating media of a known gas concentration. If a measurement of the partial oxygen pressure in liquids is needed, and if it cannot be assumed that the calibrating medium has the same optical properties as the sample, the interface between membrane and sample can be expected to show optical effects interfering with the fluorescence signal obtained. This is mainly due to the fact that the conditions of reflection at the interface between membrane and sample will depend on the optical properties of the sample medium, thus making the reflection of the excitation light and fluorescent light back into the sensor membrane dependent on the optical properties of the sample medium. This undesirable side effect may be avoided by providing the interface between membrane and sample medium with well-defined optical properties.

From German Pat. No. 25 08 637, for instance, it is known that the surface of such an optical sensor may be metal-coated or blackened such that the influence of the optical properties of the sample medium is negligible.

In measuring devices according to the present invention with a higher indicator concentration, this has proved of disadvantage, since an adequately thin blackening or sealing coat may easily be removed from the surface of the sensor, while an increase in thickness in order to gain mechanical stability would impair diffusion of oxygen from the sample area into the indicator interior.

For this purpose it is proposed in an embodiment of this invention that an additional layer of polymer of low transparency be applied on the side of the polymer carrier facing the sample, e.g., a silicone coating containing particles of ferrous oxide.

Another possibility of achieving optical independence of the sample medium is the incorporation of pigments, such as ferrous oxide particles, into the polymer membrane containing the indicator substance. By the use of external fields of force during the cure time of the membrane these particles may be driven into a part of the indicator membrane close to the surface (examples of fields of force: gravitational, electric, magnetic fields).

According to a further embodiment, optical independence of the sample medium may also be established by incorporating during polymerization a thin mesh screen of metal or plastic on the side of the polymer carrier facing the sample. The meshes used in screen printing processes have been found suitable in this context.

Although dissolving the indicator substance in the polymer carrier material will often suffice to prevent indicator losses to the environment, other methods of immobilizing the indicator substance in the polymer carrier may be preferable for various applications.

Such methods include:

(a) Restriction of indicator mobility in the polymer by chemical modification of the indicator substances (alkylation with longer C chains).

(b) Covalent bonding of the indicator substances to the polymer material.

DESCRIPTION OF A PREFERRED EMBODIMENT DEPICTED IN THE ACCOMPANYING DRAWING

In the above manner a multi-layer sensor may be built, as is shown in the enclosed drawing. A bottom layer 1 which is turned towards a lighting and light measuring device (not shown here), and is irradiated by excitation light ($h\gamma$), will serve as solid carrier (e.g. glass). A medium layer 2 is that layer of polymer that contains the fluorescent indicator in molecular distribution such that a fluorescence signal ($h\gamma'$) may be obtained depending on the oxygen content of the sample material adjacent to the sensor. Above layer 2 there is an optical insulation layer 3 facing the sample material. Layers 2 and 3 are made of a polymer material with good oxygen permeability. The above two layers are homogeneously bonded be polymerisation.

Carrier layer 1 could be dispensed with if no mechanical stability is required or if the remaining two layers are held in a suitable frame. In this case the lighting and light measuring devices are located next to layer 2.

EXAMPLES (a) In 10 ccm tetrahydrofuran, 1.5 mg pyrene, 0.3 g polyvinyl chloride and 0.7 g dinonylphthalate are dissolved in this order.

This solution is coated on a slide of acrylic glass to the amount of 30 $\mu$l per sq.cm, which is then covered with a black mesh as used in screen printing (thread diameter 30 μm, open area 46 per cent).

After evaporation of the tetrahydrofuran solvent, the sensor element will be ready for use.

(b) In 10 ccm tetrahydrofuran 1.5 mg pyrene, 0.3 g polyvinyl chloride and 0.7 g dinonylphthalate are dissolved in this order, and 5 mg ferrous oxide particles are suspended.

This suspension is applied on a slide of acrylic glass to the amount of 30 μ per sq.cm. During evaporation of the solvent the slide is within the field of a permanent magnet directing the ferrous oxide particles towards the side of the polymer layer turned away from the slide.

After evaporation of the tetrahydrofuran solvent the sensor will be ready for use.

We claim:

1. A sensor element which, when placed in contact with a sample containing oxygen, is capable of indicating the oxygen content in said sample, said sensor element comprising a carrier which is composed of a linear and amorphous polymer which is compatible with plasticizers, said polymer carrier being permeable to oxygen molecules; a plasticizer compound contained within said polymer carrier; and an oxygen-sensitive fluorescent indicator substance selected from the group consisting of polycyclic aromatic molecules, homocyclic aromatic molecules and heterocyclic aromatic molecules contained within said polymer carrier, said oxygen-sensitive fluorescent indicator substance upon excitation emitting light of a certain wavelength and of varying intensity depending on the amount of oxygen from said sample in contact therewith.

2. A sensor element according to claim 1, wherein said carrrier is composed of hydrophilic polymers selected from the group consisting of cellulose acetate, cellulose acetate butyrate, cellulose nitrate and ethyl cellulose, and wherein said plasticizers are selected from the group consisting of glycol, glycerin and pentaerythrite.

3. A sensor element according to claim 1, wherein said carrier is composed of hydrophobic polymers selected from the group consisting of polyvinylchloride, polystrene, polyvinyllacetate, polyvinyl butyral, polyvinyl chloride acetate, polyethylene, polypropylene, polyurethane, polyester, natural rubber, isoprene rubber, chloroprene rubber and butyl rubber, and wherein said plasticizers are selected from the group consisting of high-boiling esters, mineral oils, chlorinated biphenyls, chlorinated polyphenyls, epoxidized oils, polymeric plasticizers, and polymerizable plasticizers.

4. A sensor element according to claim 3, wherein said high-boiling esters are selected from the group consisting of triarylphosphates, dialkylphthalates, dialkyladipates and dialkylsebacates.

5. A sensor element according to claim 3, wherein said polymeric plasticizers are selected from the group consisting of polyester, polyisobutane and nitride rubber.

6. A sensor element according to claim 3, wherein said polymerizable plasticizers are selected from the group consisting of alkyl ester, aryl ester and nitride ester.

7. A sensor element according to claim 1, wherein said fluorescent indicator substance comprises a polycyclic aromatic hydrocarbon which displays fluorescence decay times $\tau_o$ greater than 5 ns.

8. A sensor element according to claim 1, wherein said polymer carrier defines a side which is intended to face the sample containing oxygen, and wherein said sensor element includes an additional layer of polymer of low transparency which is applied on said side of said polymer carrier.

9. A sensor element according to claim 8, wherein said additional layer has the same composition as said carrier and wherein it incorporates particles of ferrous oxide.

10. A sensor element according to claim 1, further including pigment particles in said polymer carrier.

11. A sensor element according to claim 10, wherein said pigment particles comprise ferrous oxide particles.

12. A sensor element according to claim 10, wherein said pigment particles are accumulated on the side of said polymer carrier facing said sample due to the influence of external fields of force, such as gravitational, electric or magnetic fields.

13. A sensor element according to claim 1, wherein said polymer carrier defines a side which is intended to face the sample containing oxygen, and wherein said sensor element includes a thin mesh screen embedded in said side of said polymer carrier.

14. A sensor element according to claim 1, wherein said fluorescent indicator substance includes hydrocarbon chains containing between 3 and 20 carbon atoms, such that the mobility of said fluorescent indicator substance in said polymer carrier is reduced.

15. A sensor element according to claim 1, wherein said fluorescent indicator substance is covalently bonded to said polymer carrier to immobilize it within said carrier.

* * * * *